United States Patent
Plahey et al.

(10) Patent No.: US 8,321,044 B2
(45) Date of Patent: Nov. 27, 2012

(54) MULTIMEDIA SYSTEM FOR DIALYSIS MACHINE

(75) Inventors: Kulwinder S. Plahey, Martinez, CA (US); Mohsen Reihanifam, Rancho Santa Fe, CA (US); Carlos E. Medina, Concord, CA (US); Tri Ly, Dublin, CA (US); Maureen Lyden Green, Melrose, MA (US); Thomas R. Williams, Nashua, NH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 945 days.

(21) Appl. No.: 12/394,443

(22) Filed: Feb. 27, 2009

(65) Prior Publication Data

US 2009/0222119 A1    Sep. 3, 2009

Related U.S. Application Data

(60) Provisional application No. 61/032,755, filed on Feb. 29, 2008.

(51) Int. Cl.
*G06F 17/00* (2006.01)
*H02B 1/00* (2006.01)
*C02F 1/44* (2006.01)

(52) U.S. Cl. .................. 700/94; 381/123; 210/321.7

(58) Field of Classification Search ............... 700/94; 381/123; 210/321.6, 321.7, 646; 604/4.01, 604/29
See application file for complete search history.

(56) References Cited

U.S. PATENT DOCUMENTS

| | | | |
|---|---|---|---|
| 5,324,422 A | 6/1994 | Colleran et al. | |
| 5,421,823 A | 6/1995 | Kamen et al. | |
| 5,431,626 A | 7/1995 | Bryant et al. | |
| 5,438,510 A | 8/1995 | Bryant et al. | |
| 6,503,062 B1 | 1/2003 | Gray et al. | |
| 6,808,369 B2 | 10/2004 | Gray et al. | |
| 6,814,547 B2 | 11/2004 | Childers et al. | |
| 6,929,751 B2 | 8/2005 | Bowman, Jr. et al. | |
| 7,083,719 B2 | 8/2006 | Bowman, Jr. et al. | |
| 2006/0195064 A1 | 8/2006 | Plahey et al. | 604/151 |
| 2006/0234202 A1* | 10/2006 | Brown | 434/323 |
| 2007/0104334 A1* | 5/2007 | Dallam et al. | 381/77 |
| 2007/0276183 A1* | 11/2007 | Melder | 600/112 |
| 2008/0097283 A1 | 4/2008 | Plahey | |
| 2009/0113335 A1* | 4/2009 | Sandoe et al. | 604/29 |

OTHER PUBLICATIONS

European Search Report and the European Search Opinion for Application No. EP 09 00 2867, dated Jul. 15, 2009, 8 pages.

* cited by examiner

*Primary Examiner* — Jesse Elbin
(74) *Attorney, Agent, or Firm* — Fish & Richardson P.C.

(57) ABSTRACT

This patent application relates generally to dialysis machines.

35 Claims, 5 Drawing Sheets

MULTIMEDIA SYSTEM FOR DIALYSIS MACHINE

CROSS-REFERENCE TO RELATED APPLICATIONS

This application claims priority under 35 U.S.C. §119 to U.S. Provisional Patent Application No. 61/032,755, filed on Feb. 29, 2008, the contents of which are hereby incorporated by reference in its entirety.

TECHNICAL FIELD

This patent application relates generally to dialysis machines.

BACKGROUND

Dialysis to support a patient whose renal function is inadequate is well known. Two principal dialysis methods are utilized: hemodialysis or "HD", and peritoneal dialysis or "PD."

Hemodialysis is carried out by passing the patient's blood through a usually external dialysis machine typically in a clinical setting. A hemodialysis (HD) machine contains a dialyzer with a semi-permeable membrane that allows water and waste products to pass out of the blood into a dialysate solution. The HD machine thus acts as an artificial kidney for cleansing the blood. The diffusion of water and solutes across the membrane during hemodialysis is called ultrafiltration.

Peritoneal dialysis (PD) utilizes the patient's own peritoneum, a membranous lining of the abdominal body cavity. With its good perfusion properties, the peritoneum is capable of acting as a natural semi-permeable membrane for transferring water and waste products to a type of dialysate solution known as PD solution introduced temporarily into the patient's abdominal cavity. An access port is implanted in the patient's abdomen and the PD solution is infused usually by a pump into the patient's abdomen through a patient line and left to dwell for a period of time and then drained out. This procedure is usually repeated several times for a complete treatment.

PD machines called cyclers are designed to automatically control the filling, dwelling, and draining of PD solution to and from the patient's peritoneal cavity. A PD cycler is an attractive solution for many kidney patients because it can be used at home while the patient is asleep, avoids extracorporeal blood transit, and lessens the need for visits to the clinic for hemodialysis.

A PD treatment typically lasts for several hours, and often begins with an initial drain cycle to empty the peritoneal cavity of spent dialysate. The sequence then proceeds through a succession of fill, dwell, and drain phases that follow one after the other. A PD machine can be programmed by the patient according to the doctor's prescription guidelines to vary the fill, dwell and drain times, total time and volume of fluid transferred. These are settable parameters on the PD machine's graphical user interface, usually including, e.g., a touch screen and/or keypad and control buttons.

The PD solution itself is usually sourced from a set of pre-filled bags which are connected via tubing to the machine for warming and pumping PD solution through the patient line. The machine itself includes a console with a computer and pumps and valves controlled by the computer to pull PD solution from the correct bag and pump it to the patient, and then, after a programmed interval, draw fluid out of the patient to a drain or drain bag. The fluid lines may include a removable flexible plastic cassette with pump chambers, valve elements and channels connected to the patient and drain lines and PD solution bags via tubing, as shown, for example, in pending U.S. Published Patent Applications US 2006-0195064 A1, published Aug. 31, 2006 and entitled "Portable Apparatus for Peritoneal Dialysis Therapy," and US-2007-0112297-A1, published May 17, 2007 and entitled "Cassette System for Peritoneal Dialysis Machine," both of which are incorporated herein by reference in their entirety. The cassette may be inserted into a pressurized door where it mates with the pumping mechanism and valve actuators. The cassette and its associated tubing are for one time use and are disposable after each dialysis session.

To set up a PD treatment, the patient or someone assisting the patient must generally do two things: physical set up and programming. Physical set up may involve, e.g., arranging and powering up the PD machine console on a table, for example, next to a bed where the patient will be lying, obtaining the PD solution bags and a fresh set of disposables (e.g., cassette and tubing), installing the bags and disposables correctly on the PD machine and connecting the patient line to the patient's abdominal access port. The programming part of the set up may involve, e.g., selecting the mode of operation and setting the aforementioned parameters via the PD machine's user interface, which may include a touch screen, or a combination of touch screen and keys (e.g., feathertouch keys) or buttons.

These tasks generally take a certain amount of training on any PD machine in order to correctly set up and carry out the procedure.

Likewise, to set up an HD treatment, a patient (or someone assisting the patient) must generally go through a series of steps to physically set up and program an HD machine. These tasks likewise generally take a certain amount of training on the HD machine.

SUMMARY

In general, in some aspects, a dialysis machine includes a console, a control system, a multimedia player, a memory port, and a selector video switch. The console is connectable to a patient to perform dialysis. The control system is within the console and has a controller configured to carry out a programmed dialysis therapy on the patient. The control system includes a graphical user interface that includes a display and user data entry system. The graphical user interface is configured to produce video outputs to show screens on the display for setting up and controlling dialysis parameters in response to user input commands using the data entry system. The multimedia player is in the console. The multimedia player is separate and independent from the control system. The multimedia player is configured to respond to a command signal from the graphical user interface to control the playing of a selected media file to reproduce a video on the display. The memory port is carried by the console and is operatively connected to the media player. The memory port is configured to receive a removable memory card carrying a multimedia file that can be selected and played by the multimedia player. The selector video switch is configured to alternatively supply a first video output of the control system to the display system or a second video output from the multimedia player in response to a second command signal from the control system.

Implementations may include one or more of the following features.

In the dialysis machine, the second command signal may be sent from the control system in response to a user input command received at the graphical user interface.

The dialysis machine may also include a USB data communications interface. The USB data communications interface may include a USB port and a USB interface control system. The USB port may be on the dialysis machine. The USB port may be configured to accept a USB flash memory device. The USB interface control system may be configured to manage the uploading and downloading of dialysis related data from the USB flash memory device.

In the dialysis machine, the multimedia file on the memory card may include a dialysis training video.

The dialysis machine may include a peritoneal dialysis machine. The dialysis machine may include a hemodialysis machine. The dialysis machine may include a hemodiafiltration machine. The dialysis machine may include a combined peritoneal dialysis and hemodialysis machine. The dialysis machine may include a combined peritoneal dialysis, hemodialysis, and hemodiafiltration machine.

In the dialysis machine, the multimedia player may include at least one of an Ethernet module, a USB port, or a wireless module.

In some aspects, a dialysis machine includes a console. The console is connectable to a patient to perform dialysis. The console includes a control system, a multimedia player, and a switch. The control system has a controller. The control system is configured to carry out a dialysis procedure on the patient. The control system includes a graphical user interface. The graphical user interface includes a display and user data entry system. The control system is configured to produce a video output to show screens on the display for setting up and controlling dialysis parameters in response to user input commands using the data entry system. The multimedia player is independent from the control system and is configured to respond to a command signal from the control system to control the playing of a multimedia file to reproduce a video on the display. The multimedia player is configured to select and access the multimedia file from a memory. The switch is configured to, responsive to a second command signal from the control system, alternate between supplying the video output from the control system to the display and supplying a second video output from the multimedia player to the display.

Implementations may include one or more of the following features.

In the dialysis machine, the memory may include a removable memory card that carries the multimedia file. The multimedia player may include, and may be operatively connected to, a memory port. The memory port may be configured to receive the removable memory card.

In the dialysis machine, the multimedia player may include the memory. The memory may include a non-volatile memory.

The dialysis machine may also include a USB data communications interface. The USB data communications interface may include a USB port and a USB interface control system. The USB port may be on the dialysis machine. The USB port may be configured to accept a USB flash memory device. The USB interface control system may be configured to manage the uploading and downloading of dialysis related data from the USB flash memory device.

In the dialysis machine, the multimedia file may include instructional media content.

In the dialysis machine, the instructional media content may include a dialysis training video.

The dialysis machine may include a peritoneal dialysis machine. The dialysis machine may include a hemodialysis machine. The dialysis machine may include a hemodiafiltration machine. The dialysis machine may include a combined peritoneal dialysis and hemodialysis machine. The dialysis machine may include a combined peritoneal dialysis, hemodialysis, and hemodiafiltration machine.

In the dialysis machine, the multimedia player may include at least one of an Ethernet module, a USB port, or a wireless module.

In some aspects, a method includes accessing a multimedia file from a memory using a multimedia player of a dialysis machine. The multimedia file includes a training video for operating the dialysis machine. The multimedia player is separate and independent from a dialysis control system of the dialysis machine. The dialysis machine is connectable to a patient to perform dialysis. The method also includes switching an input of a video display of the dialysis machine from an output of the dialysis control system to an output of the multimedia player. The method also includes commanding the multimedia player to start playing the multimedia file.

Implementations may include one or more of the following features.

The method may also include downloading the multimedia file onto the memory. The multimedia player may include the memory. The memory may include a non-volatile memory.

In the method, the memory may include a removable memory card external to the multimedia player and the dialysis machine. The multimedia player may include a memory card port configured to receive the removable memory card. The method may also include inserting the removable memory card into the memory card port.

The method may also include loading the multimedia file onto the memory of the removable memory card.

The method may also include, in response to a user of the dialysis machine pressing a help key on a screen of a display on the dialysis machine, playing at least part of the multimedia file such that an excerpt from the training video is shown on the display corresponding to a particular screen in order to provide assistance to the user with a particular step in a set up procedure of the dialysis machine.

In the method, the multimedia file may include a video file.

In the method, the dialysis machine may equipped with audio capability. In the method, the video display may include an LCD touch screen. The audio capability may include one or more audio speakers.

In the method, the multimedia file may include a video file and a music file. The method may also include, during dialysis therapy, playing at least part of the multimedia file to play music on one or more audio speakers of the dialysis machine.

In the method, the dialysis machine may include a peritoneal dialysis machine. The dialysis machine may include a hemodialysis machine. In the method, the dialysis machine may include a hemodiafiltration machine. In the method, the dialysis machine may include a combined peritoneal dialysis and hemodialysis machine. In the method, the dialysis machine may include a combined peritoneal dialysis, hemodialysis, and hemodiafiltration machine.

In the dialysis machine, the multimedia player may include at least one of an Ethernet module, a USB port, or a wireless module.

In some aspects, a method includes alternatively supplying to a display of a dialysis machine, in response to a command signal from a control system of a dialysis machine, a video output from the control system, or a second video output from a multimedia player of the dialysis machine. The multimedia player is separate and independent from the control system.

The dialysis machine is connectable to a patient to perform dialysis. The method also includes receiving input from a user at a graphical user interface of the control system. The method also includes selecting and accessing, at the multimedia player, a multimedia file from a memory. The method also includes playing the multimedia file to produce the second video output. The method also includes sending the command signal responsively to at least one of the input or the accessing.

Implementations may include one or more of the following features.

The method may also include downloading the multimedia file onto the memory. The multimedia player may include the memory. The memory may include a non-volatile memory.

In the method, the memory may include a removable memory card external to the multimedia player and the dialysis machine. In the method, the multimedia player may include a memory card port configured to receive the removable memory card.

In the method, the dialysis machine may include a peritoneal dialysis machine. The dialysis machine may include a hemodialysis machine. In the method, the dialysis machine may include a hemodiafiltration machine. In the method, the dialysis machine may include a combined peritoneal dialysis and hemodialysis machine. In the method, the dialysis machine may include a combined peritoneal dialysis, hemodialysis, and hemodiafiltration machine.

The details of one or more examples are set forth in the accompanying drawings and the description below. Further features, aspects, and advantages will become evident from the description, the drawings, and the claims.

DESCRIPTION OF DRAWINGS

Numbers referring to the same items in several drawings will bear the same reference numbers.

DETAILED DESCRIPTION

A PD Machine: A PD Cycler

Figure 1A:
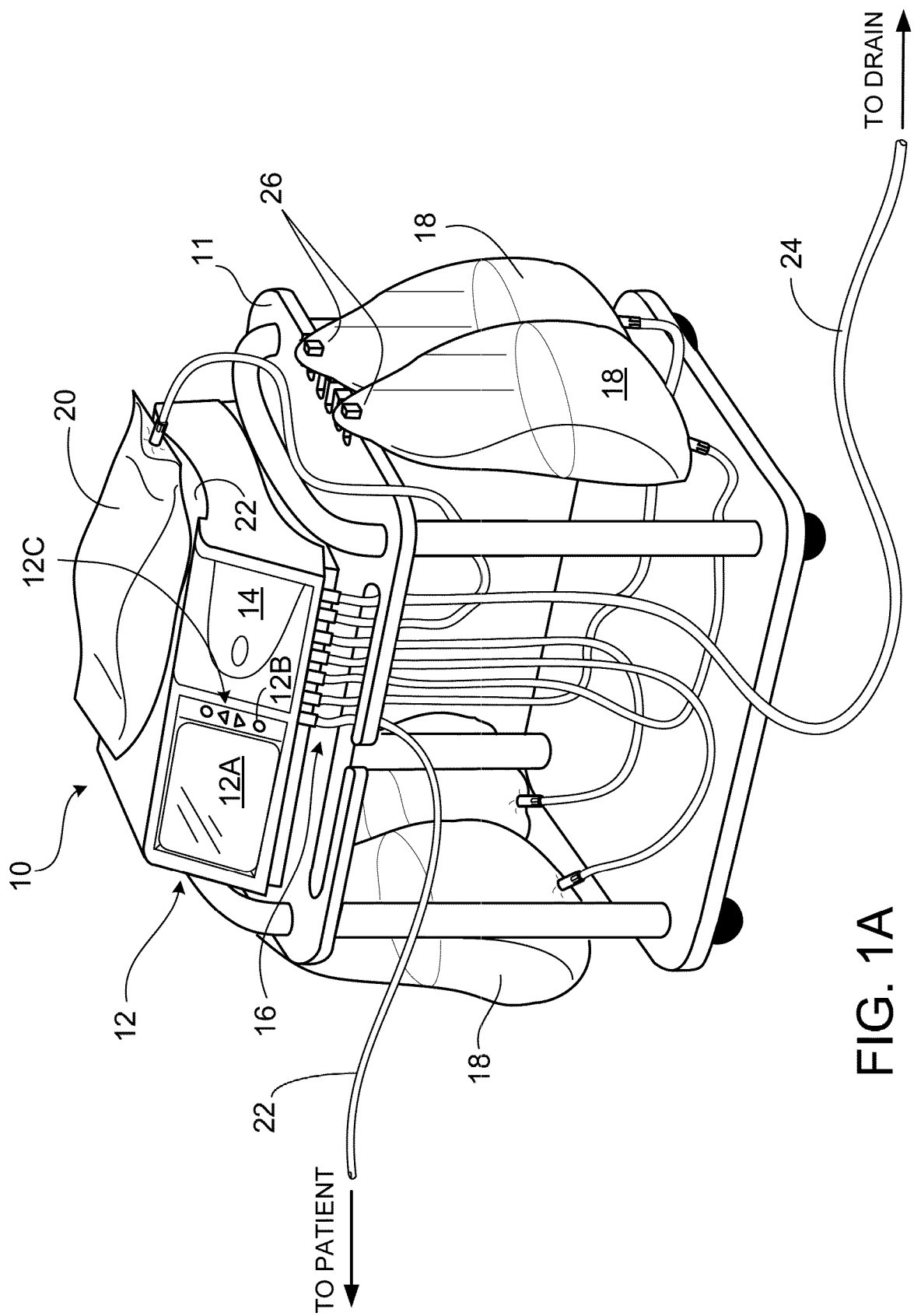
FIG. 1A is a perspective view of a PD system including a PD cycler.

In FIG. 1A, a portable PD cycler housing or console 10 is shown seated on top of a cart 11 designed to accommodate PD solution bags 18 and associated tubing. The cycler console may also be designed to be placed on a table or the like, if desired. The front of the cycler 10 includes a control panel or display 12, a display screen (e.g., a color LCD touch screen) 12A, arrow keys 12C and buttons 12B, that together furnish a graphical user interface (GUI) designed to be operated by a user, e.g., a patient, a medical assistant, or a physician. The front of the console 10 also may include a pressurized cassette compartment behind a hinged door 14. In an implementation, the disposable plastic cassette (not shown) includes channels, flexible valve domes and diaphragm-covered pumping chambers that are actuated by mating pneumatic valves and pistons interfacing with the cassette compartment to route the flow of PD solution during the fill phase from the bags through the cycler to the patient via a patient line 22 and during the drain phase from the patient to a drain or drain bag (not shown) via a drain line 24. Examples of cassettes and cassette compartments that can be used are disclosed in more detail in the above-referenced U.S. Published Patent Application US 2006-0195064 A1. The cassette itself may include tubing connectors 16 arrayed along its bottom edge. The connectors extend beneath the door 14 and are connected to tubing as shown in FIG. 1A.

As an alternative to a touch screen 12A and its associated keys 12C and buttons 12B, the cycler 10 can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

PD solution bags 18 are suspended from fingers 26 on the sides of the cart 11 as shown. A heater bag 20 is shown lying in a heater tray 22. The heater tray 22 may be formed with a shallow concave depression and may be sized and shaped to accommodate a bag 20 of PD solution, for example, a 5 liter bag of solution. The heater tray 22 may include a plurality of heating coils (not shown) embedded below the surface. The surface of the tray 22 may be slightly inclined downward to the right to assist in emptying the heater bag 20, which is arranged so that the outlet of the heater bag 20 is also at the right side, adjacent to a temperature sensor (not shown) positioned in the surface of the heater tray 22 to track the temperature of the solution in the heater bag 20 for a thermostatic control circuit that turns the heating coils on and off as needed to maintain the PD solution within a desired temperature range. The heater tray 22 may also be mounted internally on a support equipped with a load cell (not shown) to provide an electrical signal indicating the weight of the contents of the PD solution bag to tell the cycler control system how full the heater bag is with PD solution.

The PD cycler includes one or more processing devices, e.g., a central programmed microprocessor-based controller for directing the peritoneal dialysis treatment according to the programmed parameters to carry out the patient's prescribed dialysis treatment. In some implementations, the parameter entries, such as number and volume of fills, can be made on the control panel 12 of the PD cycler for a given therapy mode and the machine will then step through the procedure according to the data entered by the user, in many cases the patient. During the procedure, information concerning cycle times and volumes actually encountered may be recorded by the machine and any anomalies or error conditions or alarms generated during the procedure may be noted in the record. In certain implementations, the system is designed to record the date and time, and to create a data record of the patient's treatment.

An HD Machine

Figure 1B:
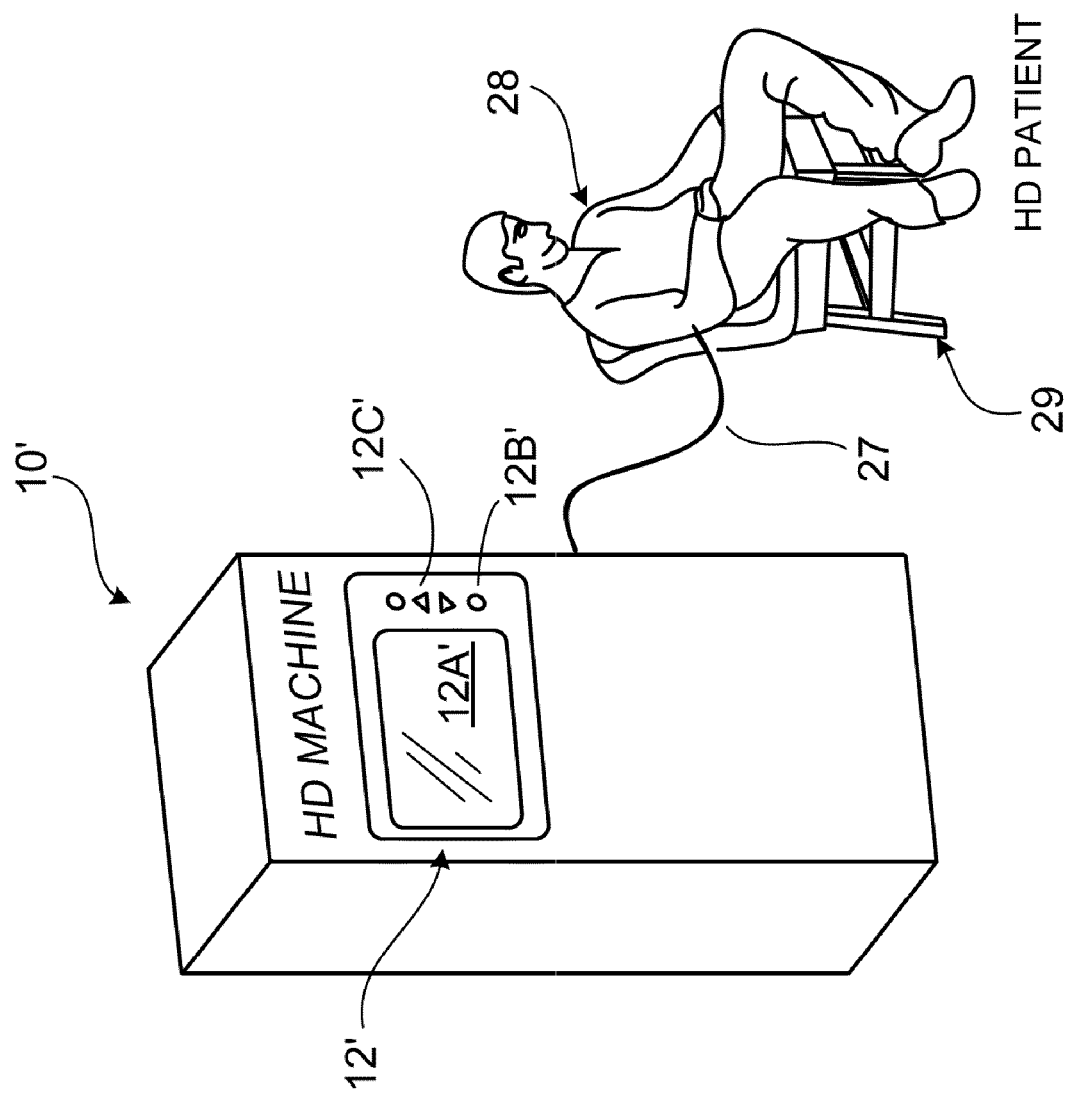
FIG. 1B is a perspective view of an HD machine in a patient care environment.

Another example of a particular type of dialysis machine, a hemodialysis (HD) machine, is shown in FIG. 1B. Hemodialysis (HD) is a process which employs a machine that includes a dialyzer to aid patients whose renal function has deteriorated to the point where their body cannot adequately rid itself of toxins. The dialyzer includes a semi-permeable membrane, the membrane serving to divide the dialyzer into two chambers. Blood is pumped through one chamber and a hemodialysis solution through the second. As the blood flows by the dialysis fluid, impurities, such as urea and creatinine, diffuse through the semi-permeable membrane into the hemodialysis solution. The electrolyte concentration of the hemodialysis fluid is set so as to maintain electrolytic balance within the patient.

Further purification in a dialyzer is possible through ultrafiltration. Ultrafiltration results from the normal situation wherein there is a positive pressure differential between the blood and the dialysis fluid chambers. This pressure differential causes water in the blood to pass through the membrane into the hemodialysis solution. This provides the benefit of reducing a hemodialysis patient's excess water load which normally would be eliminated through proper kidney functioning.

Hemodialysis is a complex treatment process in which, typically, an arterio-venous shunt, frequently termed a "fistula," is surgically inserted between a patient's artery and vein to facilitate transfer of blood from the patient to the dialyzer. During a normal hemodialysis treatment, one end of an arterial line or tube is inserted into the upstream end of the fistula (i.e., at a point near the patient's artery) and transports blood withdrawn from the upstream portion of the fistula to the inlet of the dialyzer; a venous line or tube connected to the output of the blood side of the dialyzer returns treated blood to the fistula at an insertion point downstream of the arterial line (i.e., at a point near the patient's vein).

Since hemodialysis involves removing blood from and returning blood to a patient, performing a hemodialysis procedure carries a degree of risk. Successful hemodialysis treatment generally requires monitoring of several patient vital signs and hemodialysis parameters during the hemodialysis process in order to optimize the overall efficacy of the hemodialysis procedure, to assess the condition of the fistula (the access to the patient's blood) and to determine the actual purification achieved. Some examples of parameters monitored and analyzed by a hemodialysis machine or equipment include the blood access flow rate or the rate at which blood flows out of the patient to the dialyzer, a critical parameter; and the ratio Kt/V to measure dialysis efficiency, where K is the clearance or dialysance (both terms representing the purification efficiency of the dialyzer), t is treatment time and V is the patient's total water value.

Patients undergoing hemodialysis therapy typically travel three or more times per week to hospital or dialysis treatment centers that are designed for efficient and routine hemodialysis therapy. However, technology is quickly advancing in such a way that hemodialysis therapy may be performed at home (as well as, or instead of, at a hospital or dialysis center) under the supervision of, e.g., a medical assistant, or, even by the patient undergoing the hemodialysis treatment (i.e., with or without supervision).

FIG. 1B shows an example of a patient care environment that includes an HD machine 10'. The HD machine 10' is configured for use in hemodialysis with a hemodialysis patient (HD patient) 28 seated in a chair 29 so that, e.g., the HD patient 38 may receive hemodialysis treatment from the HD machine 10'. A connector tube or arterial line 27 transports blood from the HD patient 28 to the HD machine 10' and back again to the HD patient 28 after processing and treatment in the HD machine 10'.

Like the PD cycler 10, the HD machine 10' may include a control panel or display 12', a display screen (e.g., a color LCD touch screen) 12A', arrow keys 12C' and buttons 12B, that together furnish a GUI designed to operated by a user, e.g., the HD patient, or (most often in the case of hemodialysis) a medical assistant or a physician.

As an alternative to a touch screen 12A' and its associated keys 12C' and buttons 12B', like the PD cycler 10, the HD machine 10' can include other types of screens and user data entry systems. In certain implementations, for example, the HD machine 10' includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

The HD machine includes one or more processing devices, e.g., a central programmed microprocessor-based controller for directing the hemodialysis treatment according to, e.g., programmed parameters to carry out the HD patient's 28 prescribed hemodialysis treatment. As with the PD cycler 10', in certain implementations, parameter entries can be made on the control panel 12' of the HD machine 10' for a given therapy mode. During the procedure, information regarding various HD parameters may be recorded by the HD machine 10' and any anomalies or error conditions or alarms generated during the procedure may be noted in the record. In certain implementations, the system is designed to record the date and time, and to create a data record of the HD patient's 28 treatment.

Although PD and HD machines are shown in FIGS. 1A and 1B, respectively, for ease of description, the techniques described below are explained with reference to a PD machine such as a PD cycler, and, in particular, the example PD cycler 10 shown in FIG. 1A. Of course, the techniques may be applied to other dialysis machines, such as HD machines (for example, the HD machine 10' shown in FIG. 1B), hemodiafiltration (HDF) machines, and combined PD/HD and/or PD/HD/HDF machines, for example.

Data Communications—USB port

Data may be communicated to and from the PD cycler's control system. First, data about a patient undergoing a PD procedure can be uploaded. The data may include, for example, the patient's name, ID, age, weight before the procedure and other data about the patient's personal profile, as well as the prescribed treatment. Thus, uploading of patient data could simplify the programming of a given dialysis treatment and could provide a convenient way of monitoring data about the patient.

A stored patient record may also be downloaded, e.g., following a PD treatment, to assist a user in operating the PD cycler.

The PD cycler 10 may include a Universal Serial Bus ("USB") interface that will permit the patient or physician to insert a peripheral USB device, such as a USB flash memory device with a USB interface into a USB port on the PD cycler in order to upload and download data to and from the PD cycler's control system. This can permit the user to in effect download a "data sheet" following each treatment containing, e.g., the number of cycles, fill and drain alarms, flow rates, etc., that occurred during the treatment.

On the upload side, the patient would be able to use a USB flash memory device to enter data into the PD cycler. This data could be stored on any computing device, e.g., a PC. USB ports are widely used on computing devices so that the ease and universality of use may be drastically enhanced. Thus, for example, the patient might maintain a file on his or her PC with all pertinent patient profile data along with the treatment parameters prescribed by the physician. This file could be maintained current by the patient and could include modifications in prescription made by the physician. In one scenario, the physician using a file with a standardized format and adequate security to insure integrity could e-mail the patient a prescription which the patient could then store and transfer to the USB flash drive and then use the USB flash drive to upload the data into the PD cycler. Similarly, the patient could download a data sheet about the treatment from the PD cycler onto the patient's flash drive and then transfer the data sheet to a PC and forward it as an attachment to an e-mail to his physician for inspection and logging as a permanent record.

Figure 2:
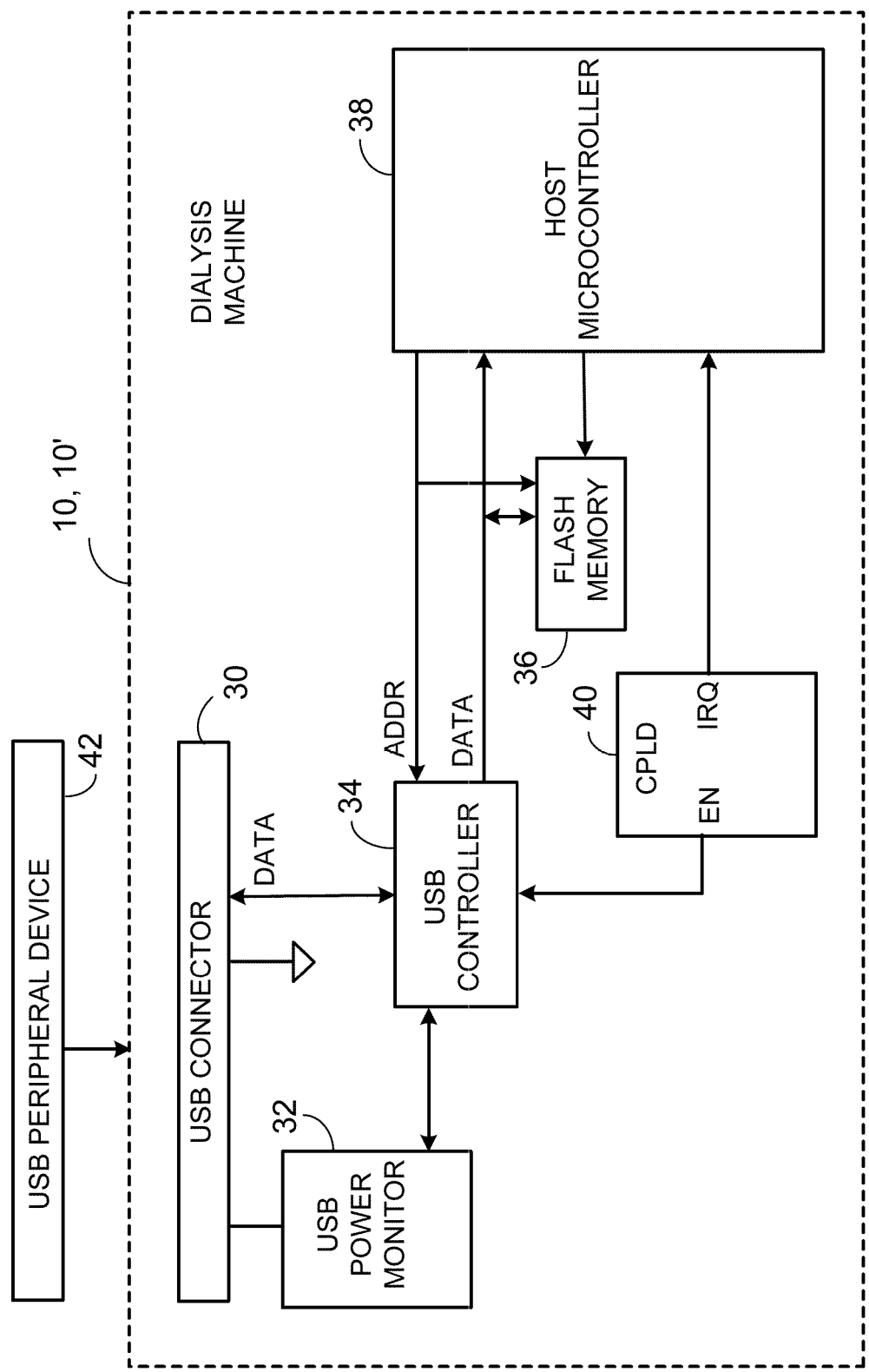
FIG. 2 is a block diagram of a USB interface system within a dialysis machine.

FIG. 2 is a block diagram of a USB interface system within a dialysis machine such as the PD cycler 10, or the HD machine 10'. The USB connector 30 can be implemented by a standard USB 2.0 port located on the back of the PD cycler housing 10 shown in FIG. 1A or any other convenient and safe location on the cycler 10. The USB connector 30 is connected to a USB power monitor 32 (e.g., a 5 volt power monitor) and to a USB controller 34 (e.g., a USB 2.0 controller with physical layer and serial interface cards) via a serial data bus (e.g., a 2-line 12 Mbs serial data bus). The USB controller 34 detects and establishes communication via a standard protocol with a USB peripheral device 42, e.g., a USB flash memory drive inserted into the USB connector 30. The USB controller 34 manages the communication sequence and buffers the data onto or off of the address and data lines (e.g., 32 bit address and data lines) as shown. The data and addressing lines may be connected to a flash memory 36 and one or more processing devices 38, e.g., a host microcontroller 38. The host microcontroller may be, e.g., Power PC microprocessor system MPC-823, which is also available to run other functions of the PD cycler 10. Other kinds of processing devices may be used on the PD cycler 10. A complex programmable logic device (CPLD) 40 may be connected between the host microcontroller 38 and the USB controller 34 to assist in processing data according to the type of data being transmitted.

Media Content: A Training Video

Because the PD cycler is designed for home use by patients without the usual assistance of medical professionals, training can be important. Two systems are described here for presenting a training video or related audio/visual material to the dialysis patient or operator on the PD cycler console 10 itself by uploading playable media files and displaying them on the LCD screen 12A of the control panel 12. This video which may accompany and complement the machine itself is easily updatable and may be designed and played for a wide target audience including nurses, doctors and patients.

Generally, media content such as a training video may be played on the PD cycler 10 and presented to a user or operator of the cycler 10. The video could be, for example, any type of image-based content in any type of digital-encoded format. This could include files with extensions such as MPG, MOV, RAM, WMV, etc. The video may contain excerpts corresponding to interactively selectable steps in the set-up procedure for the PD cycler 10, along with other types of multimedia files such as pictures or audio files for training and/or any other purposes. Generally, the content of the multimedia file (s) include(s) any multimedia type intended for training on the machine, for entertainment, or for any other purpose.

The multimedia file(s) may be stored in and accessed from any type of non-volatile memory, such as removable media like memory cards, the embedded memory of the multimedia player, or an external hard drive, such as a USB flash memory device.

A first example system makes use of the same USB interface described above with respect to FIG. 2. Referring to FIG. 2, a training video may be stored on, e.g., a USB flash drive 42 as an MPEG file, for example. The PD cycler 10 would be equipped with a built-in media player (not shown in FIG. 2). Thus, merely by inserting the flash drive 42 into the USB connector 30, the USB controller 34 under the guidance of the CPLD 40 and the microcontroller 38 would automatically unpack and play the training video using the available built-in media player and video drivers for the display 12 on the front of the cycler (FIG. 1A). Audio may be played on one or more audio speakers embedded in the cycler 10. This system of media presentation to the patient via the same control panel 12 used for parameter setting permits training to take place at home on the user's own machine and allows the physician or clinician to prescribe the correct current training video for the patient to use for the patient's particular model of PD cycler 10.

Figure 3:
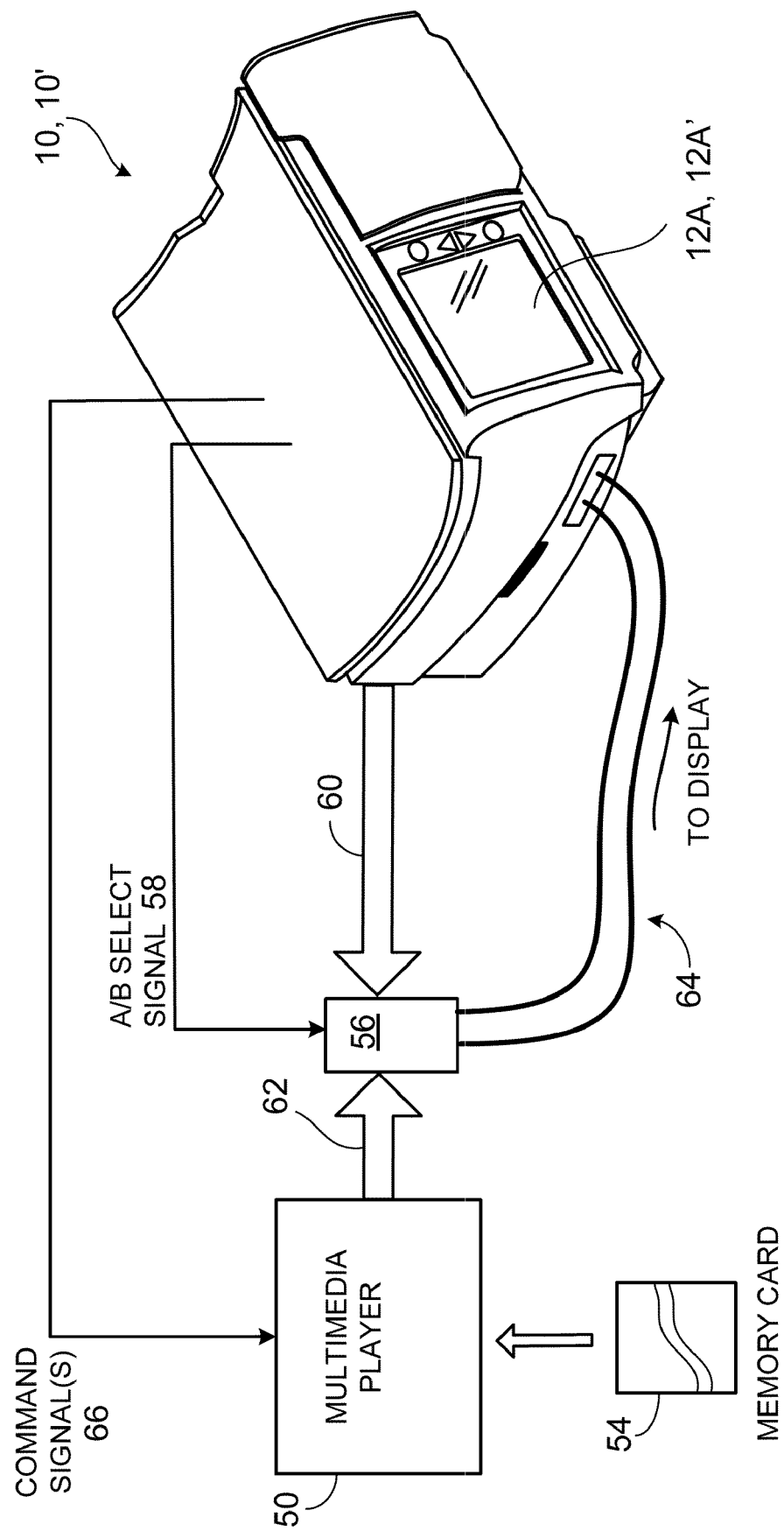
FIG. 3 is a pictorial and block diagram showing another media player system within a dialysis machine.
Figure 4:
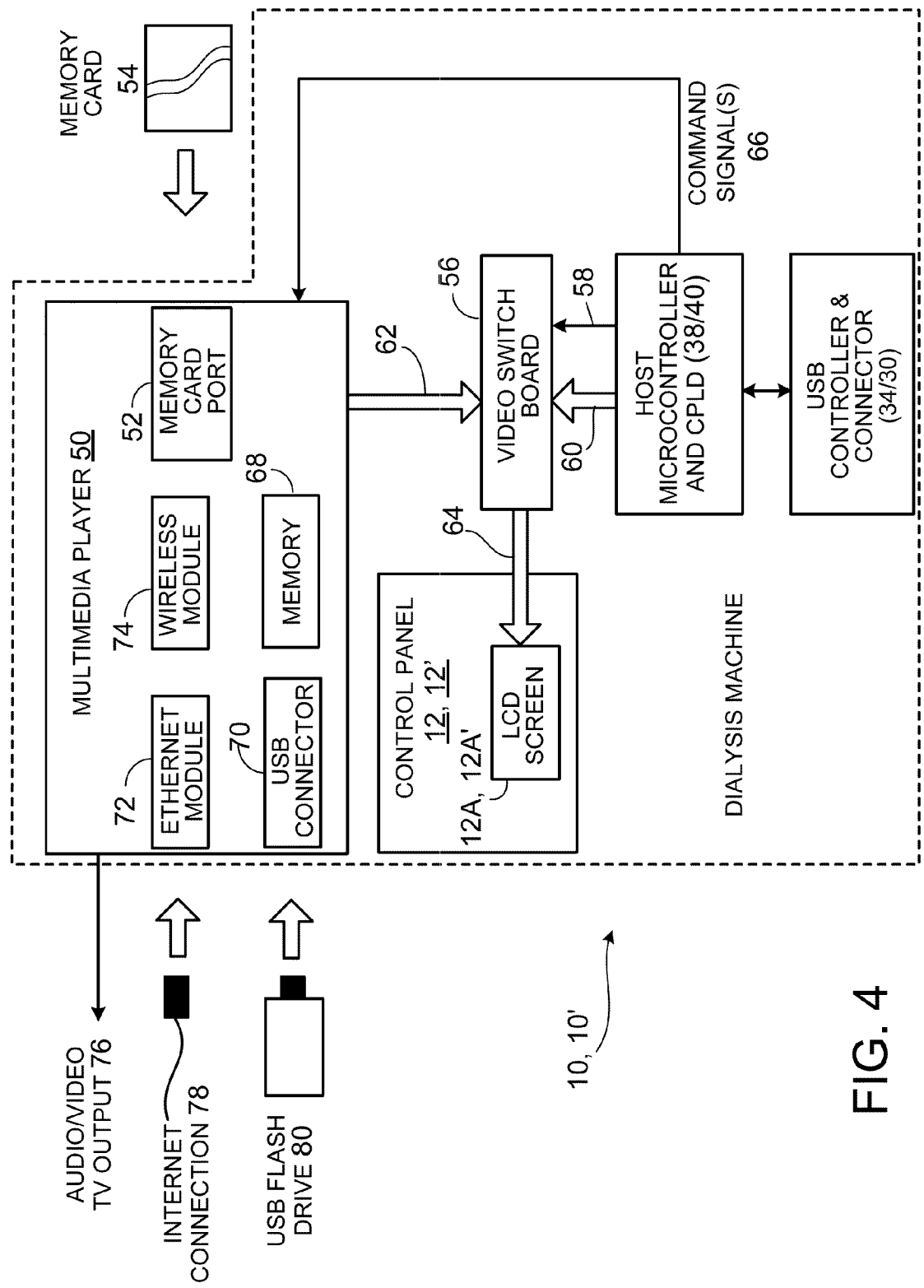
FIG. 4 is a block diagram showing the media player system and the USB interface system a dialysis machine.

A second way of presenting media content to the user via the dialysis machine console (e.g., the PD cycler console 12 or the HD machine console 12') itself is shown in FIGS. 3 and 4.

The LCD color display 12A of FIG. 1A can be in effect borrowed by a standalone video circuit on command to play a video or video excerpt stored on a standard removable memory card or internal memory of a multimedia player. This can be accomplished by adding additional circuitry for the video as shown in FIG. 3 along with minor modification of the operating software for the GUI.

In some implementations, the PD cycler 10 includes a separate multimedia player 50 for playing files stored in nonvolatile memory (e.g., internal or external to the PD cycler 10 and/or the player 50). A user at a user interface of the PD cycler 10, or the PD cycler 10 itself, may switch (via, e.g., a video switch board 56) a display input 64 for the LCD screen 12A from an output 60 (e.g., a video output) of the PD machine controller to the multimedia player 50 output 62 (e.g., video output).

In certain implementations, the PD cycler 10 is designed so that the internal multimedia player 50 of FIGS. 3 and 4 is a dedicated, autonomous, and independent part from the PD cycler circuits that are intended to take care of the PD treatment of the patient. The output 62 of the multimedia player 50 may be switched to the same display 12 used by the patient for interacting with the machine. In some implementations, the dialysis machine can take control of the display at any time (such as in the event of an emergency) and can operate without the multimedia player 50, which will generally be used in such a way that it is not indispensable for the PD treatment.

In FIG. 3, components that appear outside of the PD cycler 10 are actually intended to be included inside the PD machine. The components are illustrated as being apart from the PD cycler 10 merely to emphasize that the multimedia player 50 is independent from the dialysis system that controls and manages the PD treatment.

In this implementation as shown in FIGS. 3 and 4 a separate multimedia player 50 is provided inside the console 10. As shown in FIG. 4, the multimedia player 50 may include a memory card port 52, a memory 68 (e.g., a hard drive), a USB port 70, an Ethernet module 72, and a wireless module 74. Of course, the multimedia player 50 need not include all of these features (e.g., Ethernet, a wireless module), and may include one or more these features (e.g., only a memory card port; only a USB port and a memory; only a wireless module and a memory, etc.).

The multimedia player circuit element is provided on one of the printed circuit boards connected to the standard memory card socket or port 52 (FIG. 4), e.g., in compact flash (CF) or secure digital (SD) format receiving a standard removable memory card 54 carrying video files, e.g., in MPEG format. Thus, for example, the latest version of the appropriate training video would be supplied on a memory card. The card socket 52 may be accessible from the back of the cycler console. The multimedia files may also be stored in the built-in non-volatile memory 68 of the multimedia player 50.

The Ethernet module 72 is configured to receive an external network connection, e.g., an Internet connection 78. The USB connector 70 on the multimedia player 50 may receive a USB peripheral device such as a USB flash drive 80. The USB connector 70 can be implemented by a standard USB 2.0 port located on the media player 50. The wireless module 74 may be configured for wireless communications with e.g., the Internet, a radio access network node, or a mobile node. The multimedia player 50 may also provide audio/video TV output 76.

The video output 62 of the multimedia player 50 is passed to the video switch board 56 (FIG. 4) for the LCD screen 12a (and to circuitry for any associated speakers) via an A/B selector signal 58. The A/B video selector switch 56 alternately routes video output 60 from the GUI software for the PD cycler host controller 38 (host controller 38 and CPLD 40 as shown as a combined unit in FIG. 4 with flash memory 36 of FIG. 2 not shown), or video output 62 from the multimedia player 50 to the video switch board 56 driving the LCD screen 12A in response to the A/B select signal 58 from the controller 38. The controller 38 also provides command signal(s) 66 (e.g., a serial command signal, or a wireless signal) to start and stop the multimedia player 50 with the selected media from a desired starting location.

As shown in FIG. 4, the standalone multimedia player system can be provided along with and in addition to the USB data communication system 30, 32, 34 shown in FIG. 2 (the USB controller 34 and the USB connector 30 are shown as a combined unit in FIG. 4 with the USB power monitor 32 of FIG. 2 not shown). In this case, the standard memory port 52 may be dedicated to multimedia (such as a training video, or entertainment, etc.) and the USB connector 30 would serve for patient data and other data upload and download needs, e.g., software updates for the controller 38.

Traditional PD cyclers have displayed only text for on-screen help. The on-screen help itself is limited to displaying small messages indicating how to possibly resolve certain complications the user may encounter. The users are basically confined to reading the instruction manual which is separate from the PD cycler console.

In some implementations, implementing video on the PD cycler 10 itself may allow for the following features:

A video (e.g., connected to or originating from the Internet or another network, streaming video, or video from stored multimedia file(s) on the cycler 10) that is accessible from the main PD cycler screen 12A and instructs the user how to program the cycler for different therapy modes.

A video (e.g., connected to or originating from the Internet or another network, streaming video or video from stored multimedia file(s) on the cycler 10) that is accessible from the main PD cycler screen 12A and walks the user through the PD cycler set-up process.

A video help (e.g., connected to or originating from the Internet or another network, streaming video or video from stored multimedia file(s) on the cycler 10) that is accessible from the help button on the treatment screen to show the user what may be the cause of the problems they are encountering and showing them where to look.

Other new product information/introduction, e.g. marketing videos.

Training about renal options and/or education.

In some implementations, the main screen or start page displayed on LCD screen 12A for the set up menu may be modified to include a <help> button to allow a user to access the online video menu. Pressing the <help> button will cause the cycler to display a screen to select which video to view. For example, the screen could display the following list:

Getting Started
Learn how to program Different Therapies
Walk-thru of set-up process In an implementation, a video choice can be selected using the arrow keys to scroll through the list highlighting one at a time. Hitting the "DONE" button 12B (see FIG. 1A) would cause the cycler to activate the appropriate video via the command line to the multimedia player 50 and display the video on the screen. Pressing the <stop> button once will pause the video and pressing the <go> button will resume playing the video. Pressing the <stop> button twice will stop the video and return the user to the video choice screen. Pressing the up/down arrow keys while the video is showing will allow the user to control the volume.

Other example features that may be implemented with this system include:

Allowing the user to select different chapters of a video to display (as opposed to displaying the video from the beginning each time).

Allowing the option to play pre-stored music on the PD cycler while therapy is in progress.

Calling up and playing an ad hoc video excerpt from a particular programming or set up screen for assistance in troubleshooting, or guiding the user with a particular step in the procedure with which the user is having difficulty, or wants more guidance. This is called interactive video help.

Allowing the dialysis machine to provide a composite video output, so the multimedia content can be watched in any standard video equipment.

The interactive video help can be implemented by placing a video help icon on appropriate screens that are presented to the user/patient as he or she moves through the set-up, therapy selection and programming process screen by screen. When one of these ad hoc video help buttons is pressed, the system plays a video excerpt corresponding to the functionality associated with the screen by appropriate use of video indexing in the media.

Although the techniques described herein have been explained with reference to USB ports, USB peripheral device, etc., the techniques may be applied to other serial data port technologies, such as the IEEE (Institute of Electrical and Electronics Engineers, Inc.) 1394 High Performance Serial Bus (e.g., FireWire® of Apple® Corporation, i.LINK® of Sony® Corporation, and OHCI-Lynx® of Texas Instruments® Corporation). The techniques may be applied to technologies such as serial cable, serial ATA, RS-232, serial null modem cable, HP-IL, sync cable, enhanced mini-USB, USB on-the go, Ethernet over USB, wireless USB, USB streaming, PS/2 connections, DE-9 connectors, secure USB drives, and superspeed USB.

Although the techniques described herein have been explained with reference to a PD machine such as a PD cycler, the techniques may be applied to other dialysis machines, such as HD machines, hemodiafiltration (HDF) machines, and combined PD/HD and/or PD/HD/HDF machines, for example.

Connections may be wired and/or wireless connections. When one component is said to be connected to another component, the component may be directly connected or indirectly connected (via, e.g., still another component) to the other component.

The processes described herein and their various modifications (hereinafter "the processes"), are not limited to the hardware and software described above. All or part of the processes can be implemented, at least in part, via a computer program product, e.g., a computer program tangibly embodied in an information carrier, such as one or more computer-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subrouting, or other unit suitable for use in a computing environment. A computer program can be deployed to be executed on one computer or on multiple computers at one site or distributed across multiple sites and interconnected by a network.

Actions associated with implementing all or part of the processes can be performed by one or more programmable processing devices executing one or more computer programs to perform the functions of the processes. All or part of the processes can be implemented as, special purpose logic circuitry, e.g., an FPGA (field programmable gate array) and/ or an ASIC (application-specific integrated circuit).

Processing devices suitable for the execution of a computer program include, by way of example, both general and special purpose microprocessors, and any one or more processors of any kind of digital computer. Generally, a processing device will receive instructions and data from a read-only memory or a random access memory or both. Components of a computer include one or more processing devices for executing instructions and one or more memory devices for storing instructions and data.

Components of different implementations described herein may be combined to form implementations not specifically set forth above. Other implementations not specifically described are also within the scope of the following claims.

What is claimed is:

1. A dialysis machine, comprising
   a console connectable to a patient to perform dialysis,
   a control system within the console having a controller configured to carry out a programmed dialysis therapy on the patient,
   the control system comprising a graphical user interface that comprises a display and user data entry system, the graphical user interface configured to produce video outputs to show screens on the display for setting up and controlling dialysis parameters in response to user input commands using the data entry system,
   a multimedia player in the console, the multimedia player being separate and independent from the control system, the multimedia player being configured to respond to a command signal from the graphical user interface to control the playing of a selected media file to reproduce a video on the display,
   a memory port carried by the console operatively connected to the media player, the memory port configured to receive a removable memory card carrying a multimedia file that can be selected and played by the multimedia player, and
   a selector video switch configured to alternatively supply a first video output of the control system to the display system or a second video output from the multimedia player in response to a second command signal from the control system.

2. The dialysis machine of claim 1, wherein the second command signal is sent from the control system in response to a user input command received at the graphical user interface.

3. The dialysis machine of claim 1, further comprising:
   a USB data communications interface, comprising:
      a USB port on the dialysis machine, the USB port being configured to accept a USB flash memory device; and
      a USB interface control system configured to manage the uploading and downloading of dialysis related data from the USB flash memory device.

4. The dialysis machine of claim 1, wherein the multimedia file on the memory card comprises a dialysis training video.

5. The dialysis machine of claim 1, wherein the dialysis machine comprises a peritoneal dialysis machine.

6. The dialysis machine of claim 1, wherein the dialysis machine comprises a hemodialysis machine.

7. The dialysis machine of claim 1, wherein the multimedia player comprises at least one of an Ethernet module, a USB port, or a wireless module.

8. A dialysis machine, comprising:
   a console connectable to a patient to perform dialysis, the console comprising:
      a control system having a controller, the control system being configured to carry out a dialysis procedure on the patient, the control system comprising a graphical user interface, the graphical user interface comprising a display and user data entry system, the control system being configured to produce a video output to show screens on the display for setting up and controlling dialysis parameters in response to user input commands using the data entry system;
      a multimedia player, the multimedia player being independent from the control system and being configured to respond to a command signal from the control system to control the playing of a multimedia file to reproduce a video on the display, the multimedia player being configured to select and access the multimedia file from a memory; and
      a switch configured to, responsive to a second command signal from the control system, alternate between supplying the video output from the control system to the display and supplying a second video output from the multimedia player to the display.

9. The dialysis machine of claim 8, wherein the memory comprises a removable memory card that carries the multimedia file, and the multimedia player comprises, and is operatively connected to, a memory port configured to receive the removable memory card.

10. The dialysis machine of claim 8, wherein the multimedia player comprises the memory, and the memory comprises non-volatile memory.

11. The dialysis machine of claim 8, further comprising:
a USB data communications interface, comprising:
   a USB port on the dialysis machine, the USB port being configured to accept a USB flash memory device; and
   a USB interface control system configured to manage the uploading and downloading of dialysis related data from the USB flash memory device.

12. The dialysis machine of claim 8, wherein the multimedia file comprises instructional media content.

13. The dialysis machine of claim 8, wherein the instructional media content comprises a dialysis training video.

14. The dialysis machine of claim 8, wherein the dialysis machine comprises a peritoneal dialysis machine.

15. The dialysis machine of claim 8, wherein the dialysis machine comprises a hemodialysis machine.

16. The dialysis machine of claim 8, wherein the multimedia player comprises at least one of an Ethernet module, a USB port, or a wireless module.

17. A method, comprising: accessing a multimedia file from a memory using a multimedia player of a dialysis machine, the multimedia file comprising a training video for operating the dialysis machine, the multimedia player being separate and independent from a dialysis control system of the dialysis machine, wherein the multimedia player is configured to respond to a command signal from the control system to control the playing of the multimedia file, the dialysis machine being connectable to a patient to perform dialysis; in response to a command from the control system, switching an input of a video display of the dialysis machine from an output of the dialysis control system to an output of the multimedia player; and commanding the multimedia player to start playing the multimedia file.

18. The method of claim 17, further comprising:
downloading the multimedia file onto the memory, wherein the multimedia player comprises the memory, and the memory comprises a non-volatile memory.

19. The method of claim 17, wherein the memory comprises a removable memory card external to the multimedia player and the dialysis machine; and wherein the multimedia player comprises a memory card port configured to receive the removable memory card.

20. The method of claim 19, further comprising:
inserting the removable memory card into the memory card port.

21. The method of claim 17, further comprising:
loading the multimedia file onto the memory of the removable memory card.

22. The method of claim 17, further comprising
in response to a user of the dialysis machine pressing a help key on a screen of a display on the dialysis machine, playing at least part of the multimedia file such that an excerpt from the training video is shown on the display corresponding to a particular screen in order to provide assistance to the user with a particular step in a set up procedure of the dialysis machine.

23. The method of claim 17, wherein the multimedia file comprises a video file.

24. The method of claim 17, wherein the dialysis machine is equipped with audio capability.

25. The method of claim 24, wherein the video display comprises an LCD touch screen and the audio capability comprises one or more audio speakers.

26. The method of claim 17, wherein the multimedia file comprises a video file and a music file.

27. The method of claim 26, further comprising
during dialysis therapy, playing at least part of the multimedia file to play music on one or more audio speakers of the dialysis machine.

28. The method of claim 17, wherein the dialysis machine comprises a peritoneal dialysis machine.

29. The method of claim 17, wherein the dialysis machine comprises a hemodialysis machine.

30. The method of claim 17, wherein the multimedia player comprises at least one of an Ethernet module, a USB port, or a wireless module.

31. A method, comprising:
alternatively supplying to a display of a dialysis machine, in response to a command signal from a control system of a dialysis machine, a video output from the control system, or a second video output from a multimedia player of the dialysis machine, the multimedia player being separate and independent from the control system, the dialysis machine being connectable to a patient to perform dialysis;
receiving input from a user at a graphical user interface of the control system;
selecting and accessing, at the multimedia player, a multimedia file from a memory;
playing the multimedia file to produce the second video output; and
sending the command signal responsively to at least one of the input or the accessing.

32. The method of claim 31, further comprising:
downloading the multimedia file onto the memory, wherein the multimedia player comprises the memory, and the memory comprises a non-volatile memory.

33. The method of claim 31, wherein the memory comprises a removable memory card external to the multimedia player and the dialysis machine; and wherein the multimedia player comprises a memory card port configured to receive the removable memory card.

34. The method of claim 31, wherein the dialysis machine comprises a peritoneal dialysis machine.

35. The method of claim 31, wherein the dialysis machine comprises a hemodialysis machine.

* * * * *